United States Patent [19]

Coma Juliá

[11] Patent Number: 4,908,111

[45] Date of Patent: Mar. 13, 1990

[54] PROCESS FOR THE PREPARATION OF 7-(2-DIETHYLAMINOETHYL)-THEOPHYLLINE ACETYL SALICYLATE AND USE THEREOF

[75] Inventor: Concepción Coma Juliá, Barcelona, Spain

[73] Assignee: Laboratories Boi, S.A., Barcelona, Spain

[21] Appl. No.: 316,872

[22] Filed: Feb. 28, 1989

[30] Foreign Application Priority Data

May 5, 1988 [ES] Spain .................................. 8801377

[51] Int. Cl.$^4$ .............................................. B01J 19/08
[52] U.S. Cl. .......................... 204/157.62; 204/157.72; 204/157.89; 560/143; 544/267
[58] Field of Search ...................... 204/157.62, 157.87, 204/157.88, 157.89, 157.71, 157.72; 560/143; 544/267

[56] References Cited

FOREIGN PATENT DOCUMENTS 2096138  10/1982  United Kingdom .

*Primary Examiner*—John F. Niebling
*Assistant Examiner*—Ben C. Hsing
*Attorney, Agent, or Firm*—Scully, Scott, Murphy & Presser

[57] ABSTRACT

A process for the preparation of 7-(2-diethylaminoethyl)-theophylline acetylsalicylate and use of the product obtained. The process comprises prior filtering of a solution of the reactants through a layer of diatomaceous earth and activated carbon, cooling and treatment with a source of high frequency ultrasounds. The product is used in the manufacture of anti-agglutination and anti-thrombotic agents.

The process provides products having a high level of purity.

3 Claims, No Drawings

PROCESS FOR THE PREPARATION OF 7-(2-DIETHYLAMINOETHYL)-THEOPHYLLINE ACETYL SALICYLATE AND USE THEREOF

DESCRIPTION

The invention relates to a process for the preparation of 7-(2-diethylaminoethyl)-theophylline acetylsalicylate and the use thereof improving on the results of other known processes, such as the one described in Great Britain No. 2.096.138 to the applicant.

The invention also relates to the use of the product prepared according to the said process for the manufacture of agents having anti-agglutination and anti-thrombotic properties.

The process comprises the steps of forming a solution of acetylsalisylic acid and 7-(2-diethylaminoethyl)-theophylline in an inert solvent; filtering the said solution through a layer of diatomaceous earth and activated carbon to give a filtered solution; cooling said filtered solution to a temperature of between 1° and 8° C. and treating said solution with ultrasounds at a frequency lying between 40 and 60 KHz.

Said inert solvent is preferably tert.butylmethyl ether.

With the process described, there is obtained a product having over 99.9% chemical purity with a reaction yield of 95% of theory, m.p. 111°–113° C.

Hereafter there is given one non-limiting example of the said process.

EXAMPLE 80 g of 7-(2-diethylaminoethyl)-theophylline and 51.6 g of acetylsalicylic acid were dissolved in 2.5 liters of tert.butylmethyl ether, thereafter the solution was passed through a 40 cm long and 7 cm diameter column containing an upper layer of diatomaceous earth and a lower layer of activated carbon. The resulting solution was cooled to 5° C. and submitted to ultrasonic treatment for two hours at 50 KHz. The precipitate was filtered out and washed with 250 ml of tert.butylmethyl ether. The product was dried under vacuum at a temperature of 30° C. Thus there was obtained a practically white product, m.p. 111°–113° C. reaction yield 95%.

What I claim is:

1. A process for the preparation of 7-(2-diethylaminoethyl)-theophylline acetylsalicylate, characterised in that it comprises the steps of forming a solution of acetylsalicylic acid and 7-(2-diethylaminoethyl)-theophylline in an inert solvent, filtering said solution through a layer of diatomaceous earth and activated carbon, to give a filtered solution, cooling said solution to a temperature lying between 1° and 8° C. and treating said solution with an ultrasound source at a frequency lying between 40 and 60 KHz.

2. The process of claim 1, characterised in that said temperature is 5° C. and said frequency is 50 KHz.

3. The process of any one of the foregoing claims, characterised in that said inert solvent is tert.butylmethyl ether.

* * * * *